[54] BICYCLO HEPTANE AND BICYCLO OCTANE SUBSTITUTED INHIBITORS OF CHOLESTEROL SYNTHESIS

[75] Inventor: Bruce D. Roth, Ann Arbor, Mich.

[73] Assignee: Warner-Lambert Company, Morris Plains, N.J.

[21] Appl. No.: 439,719

[22] Filed: Nov. 21, 1989

Related U.S. Application Data

[62] Division of Ser. No. 287,813, Dec. 4, 1988, Pat. No. 4,506,657.

[51] Int. Cl.$^5$ .................. A61K 31/23; A61K 31/20; C07C 69/753; C07C 61/12
[52] U.S. Cl. .................................. 514/557; 514/469; 514/511; 514/824; 560/59; 560/118; 560/120; 562/466; 562/500; 562/502
[58] Field of Search .................. 560/118, 120, 59; 562/466, 502, 500; 514/824, 511, 532, 530, 529, 557, 469; 549/292

[56] References Cited

U.S. PATENT DOCUMENTS

| | | | |
|---|---|---|---|
| 3,983,140 | 9/1976 | Endo et al. | 549/292 |
| 4,049,495 | 9/1977 | Endo et al. | 435/933 |
| 4,137,322 | 1/1979 | Endo et al. | 514/400 |
| 4,198,425 | 4/1980 | Mistui et al. | 549/292 |
| 4,255,444 | 3/1981 | Oko et al. | 549/292 |
| 4,262,013 | 4/1981 | Mistui et al. | 549/292 |
| 4,375,475 | 3/1983 | Willard et al. | 549/292 |
| 4,647,576 | 3/1987 | Hoefle et al. | 548/453 |
| 4,681,893 | 7/1987 | Roth | 514/422 |

OTHER PUBLICATIONS

M. S. Brown & J. L. Goldstein, *New England Journal of Medicine* (1981), 305, No. 9, 515–517.
*Journal of the American Medical Association* (1984) 251, No. 3, 351–374.
F. M. Singer, et al, *Proc. Soc. Exper. Biol. Med.* (1959), 102, 370.
F. H. Hulcher, *Arch. Biochem. Biophys.* 30 (1971) 146, 422.
Brown, et al, *J. Chem. Soc. Perkin I*, (1976), 1165.

*Primary Examiner*—Richard L. Raymond
*Assistant Examiner*—Mark W. Russell
*Attorney, Agent, or Firm*—Ruth H. Newtson

[57] ABSTRACT

Certain bicyclo [2.2.1] heptane and bicyclo [2.2.2] octane substituted tetrahydro-2H-pyran-2-ones and the corresponding ring-opened acids derived therefrom are potent inhibitors of the enzyme 3-hydroxy-3-methyl-glutaryl-coenzyme A reductase (HMG-CoA reductase) and are useful as hypocholesterolemic and hypolipidemic agents.

7 Claims, No Drawings

BICYCLO HEPTANE AND BICYCLO OCTANE SUBSTITUTED INHIBITORS OF CHOLESTEROL SYNTHESIS

This application is a divisional of U.S. Ser. No. 07/287,813 filed Dec. 21, 1988, now U.S. Pat. No. 4,906,657.

BACKGROUND OF THE INVENTION

The present invention relates to compounds and pharmaceutical compositions useful as hypocholesterolemic and hypolipidemic agents. More particularly, this invention concerns bicyclo[2.2.1] heptane and bicyclo[2.2.2] octane substituted tetrahydro-2H-pyran-2-ones and the corresponding ring-opened acids derived therefrom which are potent inhibitors of the enzyme 3-hydroxy-3-methylglutarylcoenzyme A reductase (HMG-CoA reductase), pharmaceutical compositions containing such compounds, and a method of lowering blood serum cholesterol levels employing such pharmaceutical compositions.

High levels of blood cholesterol and blood lipids are conditions which are involved in the onset of arteriosclerosis. It is well known that inhibitors of HMG-CoA reductase are effective in lowering the level of blood plasma cholesterol, especially low density lipoprotein cholesterol (LDL-C), in man (cf. M. S. Brown and J. L. Goldstein, *New England Journal of Medicine* (1981), 305. No. 9, 515–517). It has now been established that lowering LDL-C levels affords protection from coronary heart disease (cf. *Journal of the Medical Association* (1984) 251. NO. 3, 351–374).

Moreover, it is known that certain derivatives of mevalonic acid (3,5-dihydroxy-3-methylpentanoic acid) and the corresponding ring-closed lactone form, mevalonolactone, inhibit the biosynthesis of cholesterol (cf. F. M. Singer, et al, *Proc. Soc. Exoer. Biol. Med.* (1959), 102, 270) and F. H. Hulcher, *Arch. Biocchem. Biophys.* 30 (1971), 146, 422.

U.S. Pat. Nos. 3,983,140; 4,049,495 and 4,137,322 disclose the fermentative production of a natural product, now called compactin, having an inhibitory effect on cholesterol biosynthesis. Compactin has been shown to have a complex structure which includes a mevalonolactone moiety (Brown, et al, *J. Chem. Soc. Perkin I*, (1976), (1165).

U.S. Pat. No. 4,255,444 to Oka, et al, discloses several synthetic derivatives of mevalonolactone having antilipidemic activity.

U.S. Pat. Nos. 4,198,425 and 4,262,013 to Mitsue, et al, disclose aralkyl derivatives of mevalonolactone which are useful in the treatment of hyperlipidemia.

U.S. Pat. No. 4,375,475 to Willard, et al, discloses certain substituted 4-hydroxytetrahydrophyran-2-ones which, in the 4(R)-trans stereoisomeric form, are inhibitors of cholesterol biosynthesis.

U.S. Pat. No. 4,647,576 to Hoelle, et al, discloses certain trans-6-[2-[(substituted)-pyrrol-1- yl]alkyl]tetrahydro-4-hydroxypyran-2-ones and the corresponding lactone ring-opened acids as inhibitor of cholesterol biosynthesis.

U.S. Pat. No. 4,681,893 to Roth discloses certain trans-6-[[(2-, 3-, or (4-carboxamido-substituted)pyrool-1-yl]alkyl- or alkenyl]tetrahydro-4-hydroxypyran-2-one inhibitors of cholesterol biosynthesis.

SUMMARY OF THE INVENTION

In accordance with the present invention, there are provided certain bicyclo[2.2.1]heptane and bicyclo[2.2.2]octane substituted tetrahydro-2H-pyran-2-ones and the corresponding ring-opened hydroxy-acids derived therefrom which are potent inhibitors of cholesterol biosynthesis by virtue of their ability to inhibit the enzyme 3-hydroxy-3-methylglutaryl coenzyme A reductase (HMG-CoA reductase).

In particular, in its broadest chemical compound aspect, the present invention provides compounds of structural Formula Ia and Ib

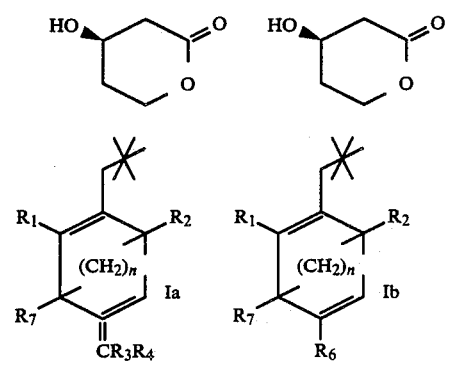

wherein X is CH2CH2— or —CH=CH—.

$R_1$ and $R_2$ independently are alkyl of from one to four carbons; alkoxy of from one to four carbons; trifluoromethyl; cyclohexylmethyl; phenyl; phenyl substituted with fluorine, chlorine, bromine, hydroxy, trifluoromethyl, alkyl of from one to four carbon atoms, or alkoxy of from one to four carbon atoms;

$R_3$, $R_4$ and $R_7$ independently are hydrogen or alkyl of from one to four carbon atoms; $R_6$ is alkyl of from one to four carbon atoms; and M is the integer 1 or 2.

Preferred compounds are those where $R_1$ is phenyl or 4-fluorophenyl, $R_2$ is methyl or isopropyl, $R_3$, $R_4$ and $R_7$ are hydrogen, $R_6$ is methyl, X is —CH=CH—, and n is 1.

Also contemplated as falling within this aspect of the invention are corresponding dihydroxy-acid compounds of Formula IIa and Formula IIb corresponding to the opened form of the lactone ring of compounds of Formula I

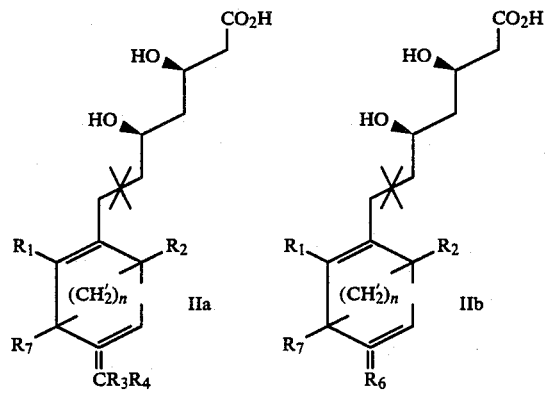

where X, $R_1$, $R_2$, $R_3$, $R_4$, $R_6$, and $R_7$ and n are as defined above, and the lower alkyl esters and the pharmaceutically acceptable salts thereof. Preferred compounds are those where $R_1$ is phenyl or 4-fluorophenyl, $R_2$ is methyl or isopropyl, $R_3$, $R_4$ and $R_7$ are hydrogen, $R_6$ is methyl, X is CH=CH; and n is 7.

In another aspect of the present invention, there is provided a method of preparing compounds of Formula Ia or Formula Ib above by (a) first reducing a compound of Formula 14a or 14b

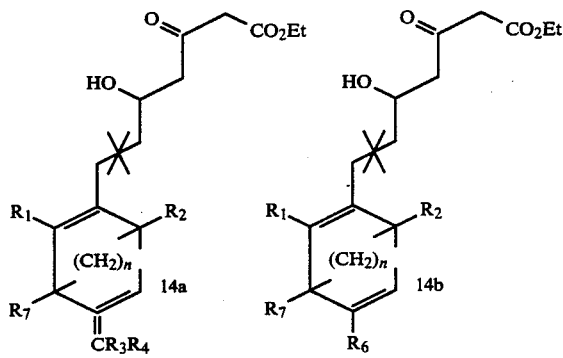

where X, $R_1$, $R_2$ and $R_3$ are as defined above, with a trialkyl-borane and sodium borohydride, (b) then oxidizing with alkaline hydrogen peroxide to produce an ester compound of Formula 15a or Formula 15b

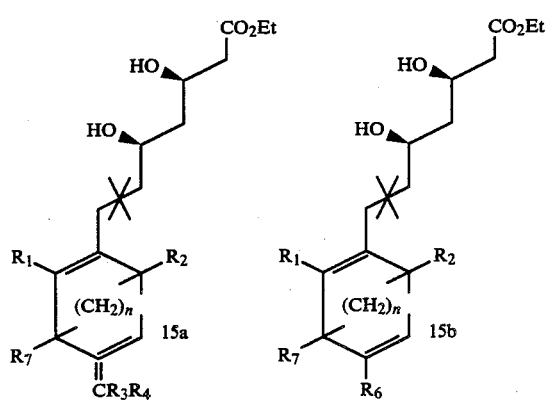

and (c) finally subjecting the ester compound to basic hydrolysis, converting the hydrolysis product to the free acid of Formula IIa or Formula IIb, and if desired cyclizing the acid to a lactone compound of Formula Ia or Formula Ib by heating in an inert solvent or, if desired, alternatively converting the acid to a lower alkyl ester or a pharmaceutically acid salt.

In another aspect, the present invention provides pharmaceutical compositions, useful as hypolipidemic or hypocholesterolemic agents, comprising a hypolipidemic or hypocholesterolemic effective amount of a compound in accordance with this invention as set forth above, in combination with a pharmaceutically acceptable carrier.

In another aspect, the present invention provides a method of inhibiting cholesterol biosynthesis in a patient in need of such treatment by administering a pharmaceutical composition in accordance with the present invention as defined above.

DETAILED DESCRIPTION OF THE PREFERRED EMBODIMENTS

In a first preferred subgeneric chemical compound aspect, the present invention provides compounds of Formula Ia and Formula Ib above wherein X is —$CH_2CH_2$—, and n, $R_1$, $R_2$, $R_3$, $R_4$, $R_6$, and $R_7$ are as defined above.

In a second preferred subgeneric chemical compound aspect, the present invention provides compounds of Formula Ia and Formula Ib above where X is —CH=CH.

As used throughout this specification and the appended claims, the term "alkyl" denotes a branched or unbranched saturated hydrocarbon group derived by the removal of one hydrogen atom from an alkane. The term "lower alkyl" denotes alkyl of from one to four carbon atoms.

The term "alkoxy" denotes an alkyl group, as just defined, attached to the parent molecular residue through an oxygen atom.

Specific examples of compounds contemplated as falling within the scope of the present invention include the following:

[4R*,6S*]-4-hydroxy-6-[2-(1-methylethyl)-5-methylene-3-phenylbicyclo [2.2.1]hept-2-en-2-yl) ethenyl]-tetrahydro-2H-pyran-2-one.

[4R*,6S*]-6-[2-(3-(4-fluorophenyl) -5-methylene I-(1-methylethyl) bicyclo [2.21]hept-2-en-2-yl) ethenyl]-tetrahydro-4-hydroxy-2H-pyran-2-one.

[4R*,6R*]-6-[2-(3-(4-fluorophenyl)-5-methyl-1-(1-methylethyl) bicyclo [2.2.1]-2,5-heptdien-2-yl) ethyl]-tetrahydro-4-hydroxy-2H-pyran-2-one.

[4R*,6S*]-6-[2-(5-ethylene-1-(4-fluorophenyl)-3-(1-methylethyl bicyclo [2.2.2]oct-2-en-2yl)ethenyl]tetrahydro-4-hydroxy-2H-pyran-2-one.

[4R*,6R*]-6-[2,(3-(4-fluorophenyl)-5-phenyl-1-trifluoromethyl bicyclo [2.2.1]-2,5-heptadien-2-yl) ethyl]tetrahydro-4-hydroxy-2H-pyran-2-one.

[4R*,6S*]-6-[2-(5-benzylidene-3-(4-fluoro-3-methylphenyl)1-(1-methylethyl) bicyclo[2.2.1]hept-2-en-2-yl) ethenyl]tetrahydro-4-hydroxy-2H-pyran-2-one.

3,5-dihydroxy-7-[3-(4-fluorophenyl)-5-methylene-1- (1-methylethyl) bicyclo [2.2.1]hept-2-en-2-yl] heptanoic acid, or a lower alkyl ester or pharmaceutically acceptable salt thereof.

3,5-dihydroxy-7-[3-cyclohexylmethyl-5-methyl- 1-(1-methylethyl)bicyclo[2.2.1]hept-2-en-2-yl]-6heptenoic acid, or a lower alkyl ester or pharmaceutically acceptable salt thereof.

3,5-dihydroxy-7-[3-(4-fluorophenyl)-5-methylene-1- (1-trifluoromethylbicyclo[2.2.2]oct-2-en-2-yl]-6- heptanoic acid, or a lower alkyl ester or pharmaceutically acceptable salt thereof.

3,5-dihydroxy-7-[3-(4-hydroxyphenyl)-1-(1-methylethylbicyclo [2.2.1]2,5-heptadien-2-yl]-6-heptenoic acid, or a lower alkyl ester or pharmaceutically acceptable salt thereof.

Compounds of the present invention in which X is —CH=CH— are prepared by the general synthetic method outlined in Reaction Scheme 1. The preparation of compounds of the present invention where X is —CH2CH2—is outlined in Reaction Scheme 2.

Reaction Scheme 1
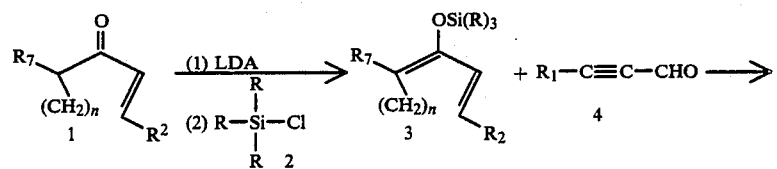
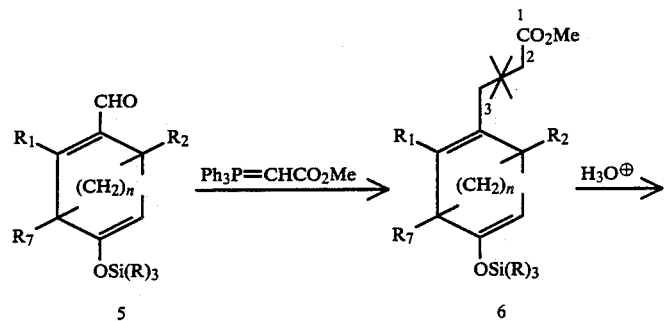
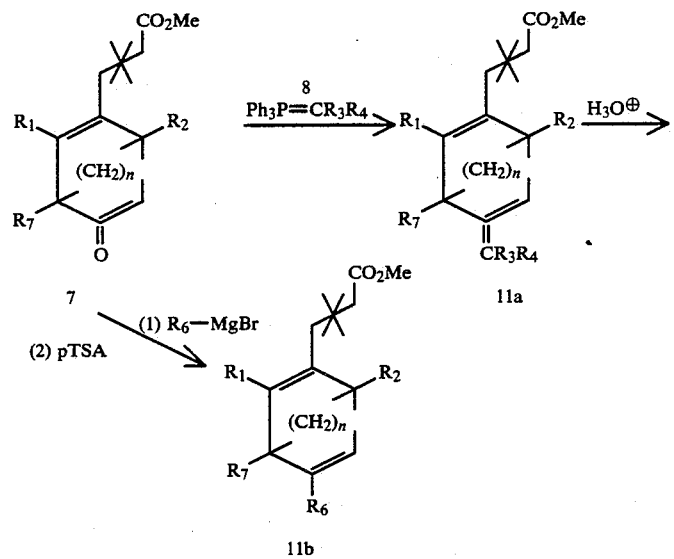
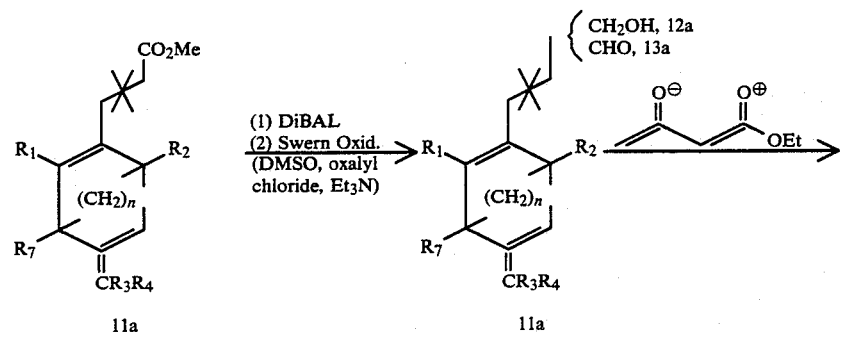

-continued
Reaction Scheme 1
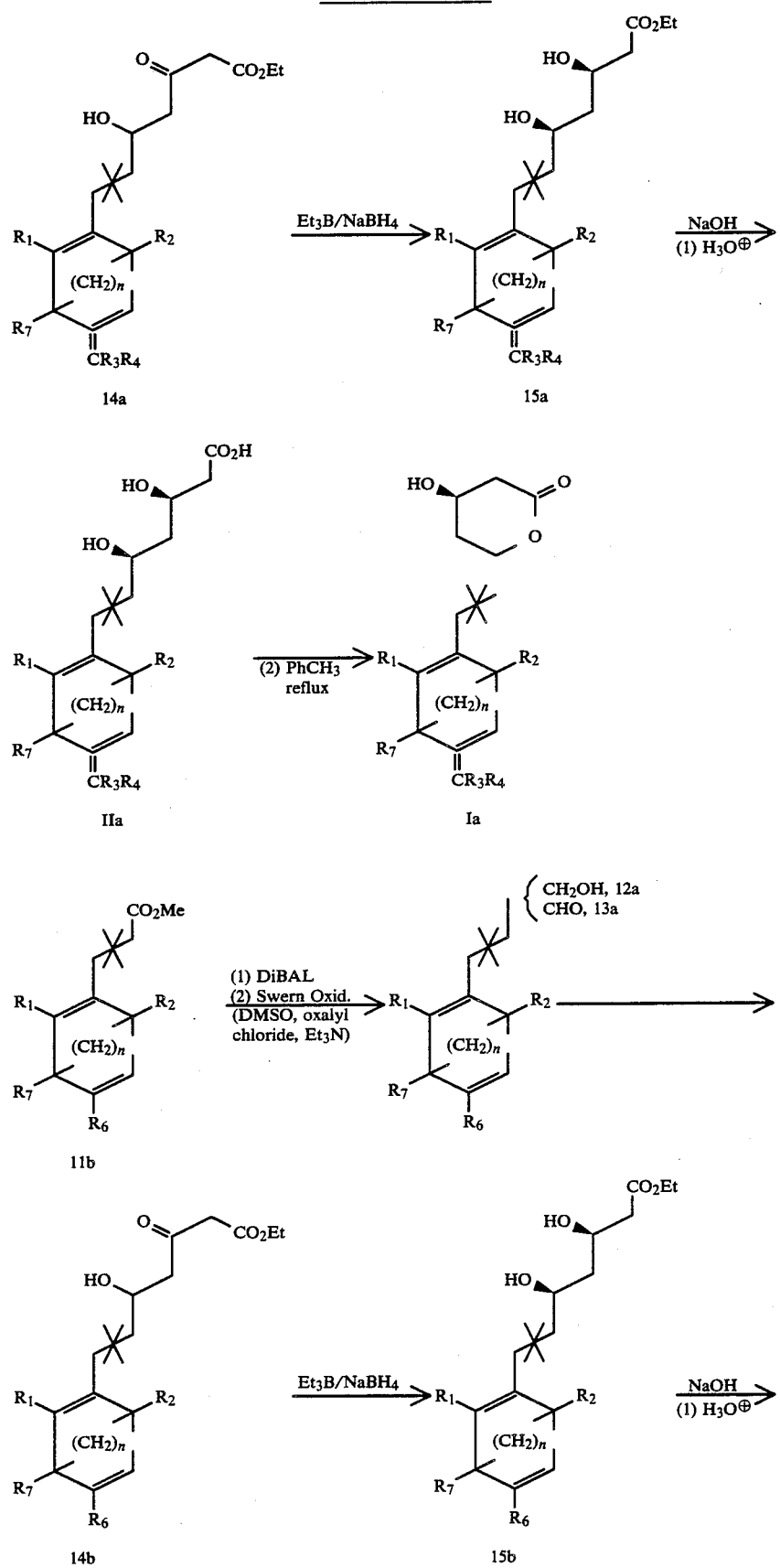

Reaction Scheme 1

-continued

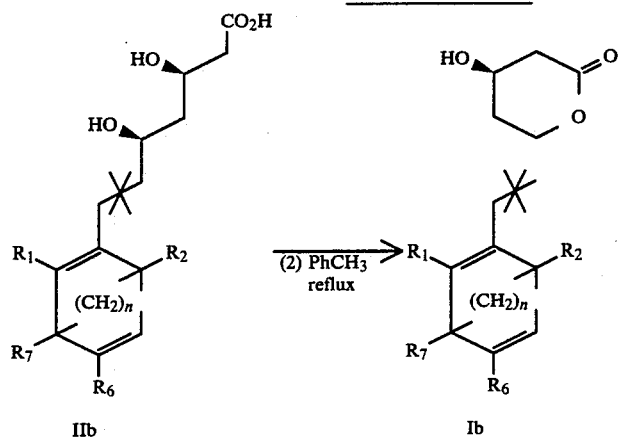

Reaction Scheme 2

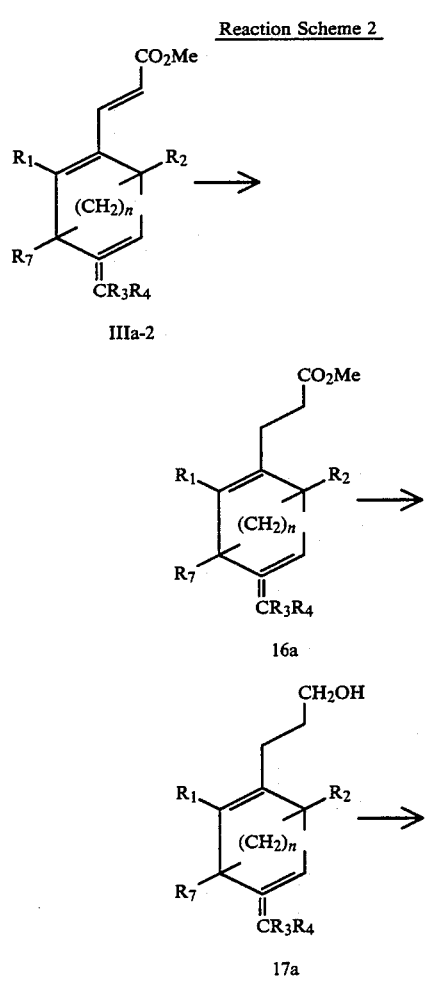

-continued
Reaction Scheme 2

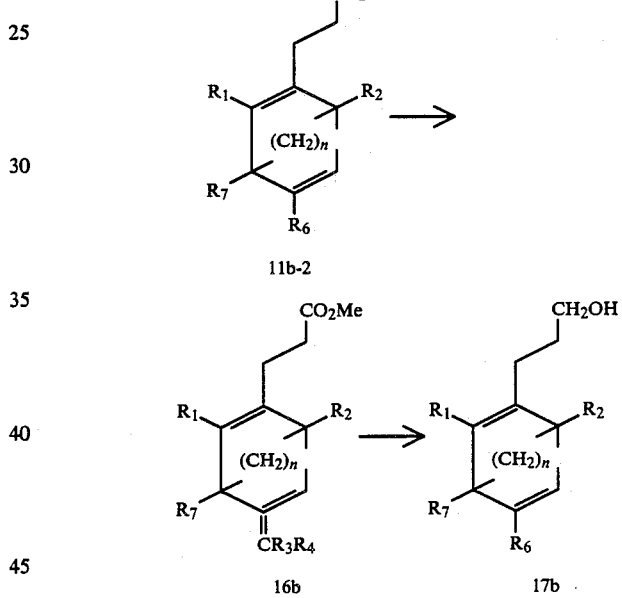

Referring to Reaction Scheme 1, the cycloalkylenone represented by 3-methyl-2-cyclopenten-1-one, 1, and t-butyldimethylsilyl chloride, 2, are reacted in an anhydrous polar solvent such as dry tetrahydrofuran at low temperature preferably between −60° C. and 80° C. under dry nitrogen.

The resulting cyclopentadiene, 3, is reacted with phenyl propargyl aldehyde, 4, in an inert solvent such as toluene to provide the 1-alkyl-3-phenyl-5-trialkyl-silyloxy-bicyclo[2.2.1] hept- 2-ene-2 carboxaldehyde, 5.

Wittig reaction of the aldehyde, 5, with an ylide such as carbomethoxy triphenylphosphorane in methylene chloride at room temperature produces the unsaturated trans-ester, 6, which is converted to the 5-oxobicycloheptene, 7 by reaction at room temperature in THF-acetic acid-water (3:1:1).

The 5-oxo compound, 7, is converted to the 5-methylene compounds, 11a. by reaction at low temperature with methylene Wittig reagent generated by reaction of methyltriphenylphosphonium bromide and butyllithium in dry ether. Alternatively, the 5-oxo compounds, 7, is converted to the 5-alkyl or 5-phenyl compound, 6, by Grignard reaction.

The ester, 11a, or 11b, is reduced by the action of DiBAL to the corresponding alcohol, 12a or 12b which in turn is oxidized by Swern oxidation to the aldehyde, 13a or 13b, which by aldol condensation to the sodium lithium dianion of ethyl acetoacetate at −7° C. in THF forms the 5-hydroxy-3-oxo-6-heptenoate, 14a or 14b.

The product of this condensation 14a. or 14b, is then reduced in a sequence of steps in which it is first dissolved in a polar solvent such as tetrahydrofuran under a dry atmosphere. A small excess of triethylborane and a catalytic amount of 2,2-dimethylpropanioic acid are next added. The mixture is stirred at room temperature for a short period, after which it is cooled to a temperature preferably between about −60° C. and −80° C. Dry methanol is added, followed by sodium borohydride. The mixture is kept at low temperature for 4–8 hours before treating it with hydrogen peroxide and ice water. The substituted 3,5-dihydroxy-6-heptenoic acid ethyl ester, 15a or 15b is isolated having the preferred R*, S* configuration.

The ester, 15a or 15b, may be utilized as such in the pharmaceutical method of this invention, or may be converted, if desired, to the corresponding acid salt form such as the sodium salt employing basic hydrolysis by generally well-known methods, and the free acid, IIa or IIb, produced by neutralization of the sodium salt can be dehydrated to the lactone, Ia or Ib, by heating in an inert solvent such as toluene with concomitant azeotropic removal of water.

Referring to Reaction Scheme 2, the unsaturated propenoate esters, 11a-2 and 11b-2 obtained by methods described above in Reaction Scheme are reduced by the action of hydrogen over Pd/C to produce the corresponding saturated propanoate ester compounds, 16a, and 16b. The saturated esters are reduced by the action of diisobutyl aluminum hydride to the corresponding alcohols, 17a and 17b, which in turn are converted through the same reaction sequence shown in Reaction Scheme 1 to the compounds of this invention.

Alternatively, the propenoate esters may be reduced directly to alcohols 17a and b by reaction with lithium aluminum hydride.

In the ring-opened dihydroxy acid form, compounds of the present invention react to form salts with pharmaceutically acceptable metal and amine cations formed from organic and inorganic bases.

The term "pharmaceutically acceptable metal cation" contemplates positively charged metal ions derived from sodium, potassium, calcium, magnesium, aluminum, iron, zinc and the like.

The "pharmaceutically acceptable amine cation" contemplates the positively charged ions derived from ammonia and organic nitrogenous bases strong enough to form such cations. Bases useful for the formation of pharmaceutically acceptable nontoxic base addition salts of compounds of the present invention form a class whose limits are readily understood by those skilled in the art. (See, for example, Berge, et al, "Pharmaceutical Salts," *J. Pharm. Sci.*, 66: 1–19 (1977).

The free acid form of the compound may be regenerated from the salt, if desired, by contacting the salt with a dilute aqueous solution of an acid such as hydrochloric acid.

The base addition salts may differ from the free acid form of compounds of this invention in such physical characteristics as melting point and solubility in polar solvents, but are considered equivalent to the free acid forms for purposes of this invention.

The compounds of this invention can exist in unsolvated as well as solvated forms. In general, the solvated forms, with pharmaceutically acceptable solvents such as water, ethanol, and the like, are equivalent to the unsolvated forms for purposes of this invention.

The compounds of this invention are useful as hypocholesterolemic or hypolipidemic agents by virtue of their ability to inhibit the biosynthesis of cholesterol through inhibition of the enzyme 3-hydroxy-3-methylglutaryl-coenzyme A reductase (HMG-CoA reductase).

The ability of compounds of the present invention to inhibit the biosynthesis of cholesterol was measured by a method (designated CSI screen) which utilizes the procedure described by R. E. Dugan, et al, *Archiv. Biochem. Biophys.*, (1972), 152, 21–27. In this method, the level of HMG-CoA enzyme activity in standard laboratory rats is increased by feeding the rats a chow diet containing 5% cholestyramine for four days, after which the rats are sacrificed.

The rat livers are homogenized, and the incorporation of cholesterol-14C-acetate into nonsaponifiable lipid by the rat liver homogenate is measured. The micromolar concentration of compound required for 50% inhibition of sterol synthesis over a one-hour period is measured, and expressed as an IC50 value.

The ability of compounds of the present invention to inhibit the biosynthesis of cholesterol was also measured by a method (designated AICS screen) which utilized the procedure described by A. W. Alberts et al, *Proc. Natl. Acad. Sci.*, (1980), 77, pp 3957–3961.

In this method male Sprague-Dawley rats (200 g body weight) previously fed 5% cholestyramine for three days were randomly divided into groups (N=5/group) and given a single dose of vehicle (controls) or compound by an oral gavage at the indicated doses. One hour after drug dosing, all rats were injected intraperitoneally with sodium [1$^{14}$C]-acetate (18.7S Ci/rat in 0.2 ml saline). After 50 minutes, blood samples were taken, plasma obtained by centrifugation, and plasma [$^{14}$C] cholesterol measured after saponification and extraction.

Activities representative of compounds in accordance with the present invention appear in Tables 1 and 2.

| X | $R_1$ | $R_2$ | $R_3$ | CSI IC$_{50}$ µMole/Liter |
|---|---|---|---|---|

-continued

| | | | | CSI IC$_{50}$ μMole/Liter |
|---|---|---|---|---|
| —CH=CH— | Ph | CH$_3$ | H | 0.44 |

TABLE 2

Structures Ia and Ib (as shown)

| X | R$_1$ | R$_2$ | R$_3$ | CSI IC$_{50}$ μMole/Liter |
|---|---|---|---|---|
| —CH=CH— | Ph | CH$_3$ | H | 0.44 |

For preparing pharmaceutical compositions from the compounds described by this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with finely divided active compound. In tablets, the active compound is mixed with the carrier having the necessary binding properties in suitable proportions and compacted in the shape and size desired.

For preparing suppository preparations, a low-melting wax such as a mixture of fatty-acid glycerides and cocoa butter is first melted, and the active ingredient is dispersed homogeneously therein, as by stirring. The molten homogeneous mixture is then poured into convenient sized molds and allowed to cool and solidify.

The powders and tablets preferably contain 5 to about 70% of the active ingredient. Suitable solid carriers are magnesium carbonate, magnesium stearate, talc, sugar, lactose, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as carrier providing a capsule in which the active component (with or without other carriers) is surrounded by a carrier, which is thus in association with it. Similarly, cachets are included. Tablets, powders, cachets, and capsules can be used as solid dosage forms suitable for oral administration.

Liquid form preparations include solutions, suspensions, and emulsions. As an example may be mentioned water or water-propylene glycol solutions for parenteral injection. Liquid preparations can also be formulated in solution in aqueous polyethylene glycol solution. Aqueous solutions for oral use can be prepared by dissolving the active component in water and adding suitable colorants, flavoring agents, stabilizers, and thickening agents as desired. Aqueous suspensions for oral use can be made by dispersing the finely divided active component in water with viscous material, i.e., natural or synthetic gums, resins, methylcellulose, sodium carboxymethyl cellulose, and other well-known suspending agents.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, and powders in vials or ampoules. The unit dosage form can also be a capsule, cachet, or tablet itself or it can be the appropriate number of any of these packaged forms.

In therapeutic use as hypolipidemic or hypocholesterolemic agents, the compounds utilized in the pharmaceutical method of this invention are administered to the patient at dosage levels of from 20 mg to 600 mg per day. For a normal human adult of approximately 70 kg of body weight, this translates to a dosage of from about 0.5 mg/kg to about 8.0 mg/kg of body weight per day.

The dosages, however, may be varied depending upon the requirements of the patient, the severity of the condition being treated, and the compound being employed. Determination of optimum dosages for a particular situation is within the skill of the art.

The following examples illustrate particular methods for preparing compounds in accordance with this invention. These examples are illustrative and are not to be read as limiting the scope of the invention as it is defined by the appended claims.

EXAMPLE 1

Preparation of 2-Tert-butyldimethylsilyloxy-4-methyl-cyclopentadiene n-Butyl lithium (65.6 m) of 1.6 M hexane solution, see J.A.C.S. 103, 6677, 1981) was added dropwise to a stirred solution of i-pr2NH (15.4 ml, 110 ml, Aldrich) in dry THF(50ml distilled from ketyl), stirring at −78° C. under dry nitrogen. The solution was stirred 30 minutes (suspension formed) and then 3-methyl-2-cyclopenten-1-one (9.89 ml, 100 millimoles, Aldrich) in 50 ml of anhyd. THF was added dropwise over 30 minutes. The light yellow solution was stirred 30 minutes and then t-BuMe$_2$SiCl (17.3 g, 115 millimoles, Aldrich) in 30 ml of anhyd. THF was added rapidly (ca.1min). The mixture was then allowed to warm slowly to room temperature and stirred overnight. It was then poured into ether and hexane washed with bicarbonate, brine, and dried (MgSO$_4$). Filtration and concentration provided 15 g of silyl enol ether; 90 MHz NMR (CDCl$_3$) δ 0.13 (S,6H), 0.95 (S,9H), 1.95 (M,3H), 2.7 (M,2H), 4.9) (M,1H), 5.78 (M,1H).

EXAMPLE 2

Preparation of 1-Methyl-3-phenyl-5-tert-butyldimethyl-silyloxy-bicyclo[2.2.1]hept-2-ene-2-carboxaldehyde A solution of the diene (Example 1, 12.3 g, 58.5 mmol.), phenyl propargyl aldehyde (7.34 ml, 60 mmol) and hydroquinone (20 mg) was stirred at room temp. in 50 ml of toluene for 24 hours. Concentration afforded 19 g of pure Diels-Alder adduct which was taken on without further purification.

EXAMPLE 3

Preparation of Methyl-3-(1-methyl-5-oxo-3-phenylbicyclo [2.2.1]hept-2-en-2-yl) propenoate A solution of the aldehyde (19.8 g, 58.1 mmoles) and methyl(triphenylphosphoranylidene)acetate (29.16 g, 87.2 mmoles) in 100 ml. $CH_2Cl_2$ was stirred and heated at reflux overnight. An NMR analysis of an aliquot indicated that some starting material remained such that 4.86 g, (14.5 mmoles) of the ylide were added. Reflux was continued for 6 hours. The cooled solution was concentrated, taken up in $PhCh_3$ and filtered to remove P(phenyl)$_3$. The filtrate was concentrated and the residue dissolved in 400 ml. of 3:1:1 THF-HoAc-$H_2O$ and stirred at room temperature for 6 hours. It was concentrated and partitioned between ether and water (500 ml each). The organic layer was washed with $H_2O$, bicarbonate, brine and dried ($MgSO_4$). Flash chromatography provided 7 g of the pure ketone.

EXAMPLE 4

Preparation of Methyl -3-(1-methyl-5-methylene-3-phenyl bicyclo [2.2.1]hept-2-en-2-yl) propenoate N-BuLi (2.6 ml of 1.6 M) was added dropwise to a stirred suspension of methyl triphenylphosphonium bromide (1.43 g) in 10 ml of ether at 25° C. The light orange solution which resulted was stirred for 30 minutes, cooled to −78° C., and methyl-2-[2-(1-methyl-3-phenyl-5-oxo-bicyclo[2.2.1 ]hept-2-enyl)]propenoate (1.0 g) in 10 ml of ether was added dropwise. The mixture was stirred briefly at −78° C., then allowed to warm slowly to room temperature. It was stirred a further 1.5 hrs at room temperature, diluted with ethyl acetate and poured carefully into water. The layers were separated and the aqueous layer extracted with ethyl acetate. The combined organic layers were washed with brine, dried ($MgSO_4$), filtered and evaporated. Flash chromatography (2x) on silica gel eluting with hexane-ethyl acetate (50:50 v/v) afforded 0.51g (51%) of the desired product.

EXAMPLE 5

Preparation of 1-methyl-5-methylene-2-[3-(2-propen-1-olyl)]-3-phenyl-bicyclo [2.2.1 hept-2-ene A solution of methyl-3-(1-methyl-5-methylene-3-phenyl-bicyclo [2.2.1]hept-2-en-2-yl)propenoate (1.66g) in dichloromethane (50 ml) was cooled to −78° C. and DiBAL (16 ml of a 1M dichloromethane solution) was added dropwise. The solution was stirred for 90 minutes at −78° C. and then a further 5 ml of DiBAL were added. The solution was stirred for 30 minutes, then quenched by addition of a saturated aqueous solution of $Na_2SO_4$. The mixture was filtered through Celite (filter cell), dried ($MgSO_4$), filtered, and evaporated to provide 1.28 g (86%) of the alcohol as a liquid.

IR (film) 3300, 2931, 1661, 1600, 1492, 766, 700 cm$^{-1}$

200 MHz NMR (CDC13) 1.5 (M,1H), 1.57 (S,3H), 1.77 (M,1H), 2.20 (M,2H), 3.40 (S,1H), 4.16 (dd,1H, J=16, 1Hz), 4,78 (s,1H), 5.08 (S,1H), 6.10 (dt, 1H, J=16, 6 Hz), 6.42 (d, 1H, J=16 Hz), 7.30 (M,5H).

EXAMPLE 6

Preparation of 3-(1-methyl-5-methylene-3-phenyl-bicyclo[2.2.1]hept-2-en-2-yl)-2-propen-1-al Dimethylsulfoxide (1.4 ml) was added dropwise to a stirred solution of oxalyl chloride (0.80 ml) in 25 ml of dichloromethane ($CH_2Cl_2$) cooled to −78° C. under dry nitrogen. The mixture was stirred for 10 minutes and then a solution of the alcohol (1.54 g) in $CH_2Cl_2$ (30 ml) was added dropwise. The mixture was stirred 30 minutes, $Et_3N$ was added (5 ml), and the cooling bath was removed. The mixture was stirred for 10 minutes, quenched with $NH_4Cl$ (sat'd aq.), and stirred for 90 minutes at room temperature. The layers were separated and the organic layer washed with brine, dried ($MgSO_4$), filtered, and evaporated. Two chromatographies (silica gel eluting with 4:1 v/v hexane-ethyl acetate) afforded 0.57 g of pure aldehyde; IR (film) 1677, 1604, 1126, 769, 701 cm$^{-1}$.

200 MHz NMR (CDCl$_3$) 15.3 (brdd, 1H, J=8, 1Hz), 1.63 (S, 3H), 1.88 (M, 1H), 2.06 (br d, 1H, J=16 Hz), 2.30 (dd, 1H, J=15, 2Hz), 3.54 (S,1H), 4,85 (S, 1H), 5.12 (t, 1H, J=1 Hz), 6.45 (dd, 1H, J=16, 8 Hz), 7.4 (m, 6H), 9.45 (d, J=8 Hz).

EXAMPLE 7

Preparation of Ethyl, 5-hydroxy-7-(1-methyl-5-methylene-3-phenyl bicyclo [2.2.1] hept-2-en-2-yl)-3-Oxo-6-heptenoate Ethyl acetoacetate (0.87 g) was added dropwise to a stirred suspension of sodium hydride (0.31 g, 60% in oil) in THF at 0° C. The mixture was stirred for 15 min. after gas evolution was complete, then n-BuLi (1.5 mL of a 1.6 M hexane solution). The mixture was stirred a further 30 minutes at 0° C., then cooled to −78° C. A solution of 3-(1-methyl-5-methylene-3-phenylbicyclo [2.2.1]hept-2-en-2-yl) -2-propen-1-al (0.57 g) in dry THF (15 mL) was added dropwise. The solution was stirred 30 minutes at −78°, warmed to 0° C. and quenched by addition of 2 mL of acetic acid. The mixture was partitioned between ethyl acetate and sat'd aq. $NaHCO_3$ and the layers were separated. The aqueous layer was further extracted with ethyl acetate and the combined organic extracts were washed with brine and dried ($MgSO_4$). Filtration and concentration provided an oil which was flash chromatographed on silica gel eluting with 4:1 v/v hexane-ethyl acetate. This provided 0.54 g (62%) of the product as a yellow oil; IR(film) 3500, 1742, 1716, 701 cm. 200 MHz NMR (CDC13) δ 1.28 (M,3H), 1.44 (M,1H), 1.54 (S,3H), 1.76 (M,1H), 2.10 (M,2H), 2.75 (M,2H), 3.40 (S,1H), 3.47 (2 singlets, 2H), 4.23(M,2H), 4.60 (M,1H), 4.78 (S,1H), 5.07 (brS,1H), 5.90 (M,1H), 6.45 (d,1H, J=16 HZ), 7.30 (M,5H).

EXAMPLE 8

Preparation of Ethyl, 3,5-dihydroxy-7-(1-methyl-5-Methylene-3-phenylbicyclo [2.2.1]hept -2-en-2-yl]-6-heptenoate Pivalic acid (0.029g) and $Et_3B$ (1.5 ml of 1M THF) were mixed in 15 mL of dry THF and stirred for 60 minutes at room temperature (RT). To this solution was added a solution of ethyl, 5-hydroxy-7-(1-methyl-5-methylene-3-phenylbicyclo [2.2.1]hept-2-en-2-yl]6-heptenoate (0.52 g) in 2mL of dry THF. After stirring for 1 hour, the solution was cooled to -78.C and $CH_3OH$ (0.5 ml) and $NaBH_4$ (0.066g) were added. The mixture was stirred 4 hours at −78°, then poured into 10 ml of 30% $H_2O_2$ cooled to 0° C. The vigorously stirred mixture was allowed to warm to RT overnight and extracted with ethyl acetate. The organic extracts were washed with $H_2O$ (3x), brine, dried ($MgSO_4$, filtered and concentrated. Chromatography on silica gel eluting with hexane - ethyl acetate (4:1 v/v) afforded 0.32 g of product; IR (film) 3500, 2932, 1735 $cm^{-1}$.

200 MHz NMR ($CDCl_3$) δ 1.30 (M,3H), 1.45 (M,1H), 1.56 (S,3H), 1.80 (M,3H), 2.10 (M,2H), 2.48 (M,2H), 3.40 (S,1H), 3.70 (br S, 1H), 4.17 (M,3H), 4.33 (M,1H), 4.78 (S,1H), 5.07 (M,1H), 5.87 (M,1H), 6.39 (d,1H, J=16Hz), 7.25 (M,5H).

EXAMPLE 9

Preparation of Sodium, 3,5-dihydroxy-7-(1-methyl-5-methylene-3-phenylbicyclo [2.2.1]hept-2-en-2-yl]-6-heptenoate The ester product of Example 8 (0.163 g) was taken up in ca. 3 ml of methanol, 0.50 ml 1 M NaOH was added, the solvent was removed in vacuo, water was added and the mixture was freeze-dried to provide the title heptenoate salt product; IR (KBr) 3500, 1581 $cm^{-1}$

EXAMPLE 10

Preparation of [4R*, 6R*]-4-Hydroxy-6-[2-(1-methyl-5-methylene-3-phenyl bicyclo [2.2.1]hept-2-en2-yl) ethenyl] tetrahydro-2H-pyran-2-one Sodium hydroxide (04. ml, 1M) was added to a solution in 2 mL methanol of 0.147 g. of the ester product of Example 9, the resulting solution was stripped on the rotary, made acid with citric acid, partitioned between ethyl acetate and $H_2O$, dried over $MgSO_4$, filtered and concentrated. The residue was taken up in $CH_2Cl_2$ and 0.090 g of dicyclohexylcarbodiimide was added at room temperature. The mixture was stirred overnight at RT, concentrated, then chromatographed on silica gel (20-230) using 50/50 hexane/ethyl acetate as eluant. Combination of the appropriate fractions gave 0.1098 g (88%) of the title product. This material was purified by taking it up in ether and filtering and concentrating the solution to dryness; IR (film): 3500, 1719, 1037, 414 $cm^{-1}$.

200 MHz NMR ($CDCl_3$): δ 1.25 (M,1H), 1.48 (M,2H) 1.55, 1.56 (2S, 3H), 1.6–2.3 (M,6H), 2.70 (M,2H), 3.40 (S, 1H), 4.38 (M, 1H), 4.80 (S,1H), 5.10 (M,2H), 5.93 (dd, 1H, J=1.6, 7.5 Hz), 6.44 (dd, 1H, J= 16, 3Hz), 7.30 (M,5H).

I claim:
1. A compound of structural Formula IIa or Formula IIb

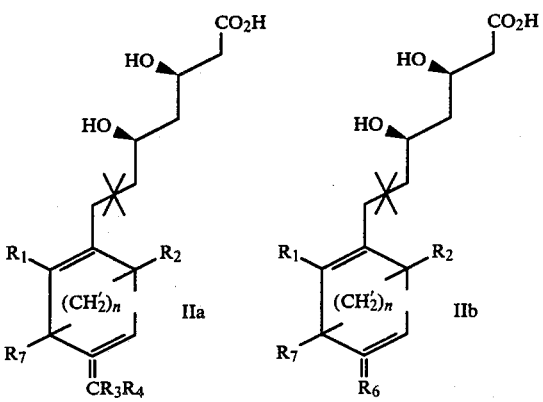

wherein X is $-CH_2CH_2-$ or $-CH=CH-$;
$R_1$ and $R_2$ independently are alkyl of from one to four carbons;
trifluoromethyl;
cyclohexylmethyl;
phenyl; or
phenyl substituted with
  fluorine,
  chlorine,
  bormine;
  hydroxy,
  alkyl of from one to four carbon atoms, or
  alkoxy of from one to four carbon atoms;
$R_3$, $R_4$ and $R_7$ independently are hydrogen or alkyl of from one to four carbon atoms;
$R_6$ is alkyl of from one to four carbon atoms or phenyl;
n is the integer 1 or 2; or
a lower alkyl ester or pharmaceutically acceptable salt thereof.

2. A compound as defined by claim 1 having the name 3,5-dihydroxy-7-[3-(4-fluorophenyl)-5-methylene-1-(1-methylethyl)bicyclo[2.2.1]hep-2-en-2-yl]-6-heptenoic acid, or a pharmaceutically acceptable salt thereof.

3. A compound as defined bY claim 1 having the name 3,5-dihydroxy-7-[3-cyclohexylmethyl-5-methyl-1-(1-methylethyl)bicyclo[2.2.1]hep-2-en-2-yl]-6-heptenoic acid, or a pharmaceutically acceptable salt thereof.

4. Compound as defined by claim 1 having the name 3,5-dihydroxy-7-[3-(4-fluorophenyl)-5-methylene-1-trifluoromethylbicyclo[2.2.2]oct-2-en-2-yl]-6-heptenoic acid, or a pharmaceutically acceptable salt thereof.

5. A compound as defined by claim 1 having the name 3,5-dihydroxy-7-[3-(4-hydroxyphenyl)-1-(1-methylethyl)bicyclo[2.2.1]2,5-heptadien-2-yl-6-heptenoic acid.

6. A pharmaceutical composition for inhibiting cholesterol biosynthesis comprising an effective amount of a compound as defined by claim 1 in combination with a pharmaceutically acceptable carrier.

7. A method of inhibiting cholesterol biosynthesis in a patient in need of said treatment comprising administering a cholesterol synthesis inhibiting amount of a compound as defined by claim 1 in combination with a pharmaceutically acceptable carrier.

* * * * *